United States Patent
Hahr et al.

(10) Patent No.: US 10,335,307 B2
(45) Date of Patent: Jul. 2, 2019

(54) PENILE CONSTRICTION DEVICE

(75) Inventors: Meike Hahr, Hamburg (DE); Heiko Tullney, Hamburg (DE)

(73) Assignee: OVO JOINT VENTURE LLC, Hightstown, NJ (US)

( * ) Notice: Subject to any disclaimer, the term of this patent is extended or adjusted under 35 U.S.C. 154(b) by 505 days.

(21) Appl. No.: 14/397,839

(22) PCT Filed: Apr. 30, 2012

(86) PCT No.: PCT/EP2012/057898
§ 371 (c)(1),
(2), (4) Date: Jul. 15, 2015

(87) PCT Pub. No.: WO2013/164006
PCT Pub. Date: Nov. 7, 2013

(65) Prior Publication Data
US 2015/0313749 A1    Nov. 5, 2015

(51) Int. Cl.
A61F 5/41 (2006.01)
A61H 19/00 (2006.01)
A61H 23/02 (2006.01)

(52) U.S. Cl.
CPC .............. *A61F 5/41* (2013.01); *A61H 19/34* (2013.01); *A61H 19/50* (2013.01); *A61H 23/0263* (2013.01); *A61F 2005/414* (2013.01); *A61F 2005/418* (2013.01); *A61H 19/32* (2013.01); *A61H 2201/165* (2013.01); *A61H 2201/1685* (2013.01)

(58) Field of Classification Search
CPC ........ A61H 19/32; A61H 19/34; A61H 19/50; A61H 2201/165; A61H 19/30; A61H 19/40; A61F 5/41
See application file for complete search history.

(56) References Cited

U.S. PATENT DOCUMENTS

| | | | |
|---|---|---|---|
| 2003/0181835 A1* | 9/2003 | Klein | A61H 19/34 601/72 |
| 2011/0034837 A1* | 2/2011 | Lee | A61H 19/44 601/46 |
| 2012/0178990 A1* | 7/2012 | Astin | A61H 19/00 600/41 |
| 2012/0271101 A1* | 10/2012 | Tan | A61F 2/50 600/38 |
| 2013/0158446 A1* | 6/2013 | Nan | A61H 19/34 601/46 |

FOREIGN PATENT DOCUMENTS

| | | |
|---|---|---|
| DE | 10229183 | 1/2004 |
| WO | WO2008003980 | 1/2008 |
| WO | WO2011077126 | 6/2011 |

* cited by examiner

*Primary Examiner* — Christine H Matthews
(74) *Attorney, Agent, or Firm* — Richard E. Oney; Venjuris, P.C.

(57) ABSTRACT

A penile constriction device comprises a ring-shaped body and a head element protruding away from the ring-shaped body. The head element is dimensioned to contact and stimulate a clitoris during sexual intercourse when the ring-shaped body is positioned on the penis.

20 Claims, 3 Drawing Sheets

PENILE CONSTRICTION DEVICE

The present invention relates to a penile constriction device comprising a ring-shaped body.

Penile constriction devices comprising a ring-shaped body adapted to encircle the penis closely adjacent the base thereof and adjacent the user's body are known in the prior art. They act by constricting the flow of blood within the organ in a selective manner so that relatively easy flow of blood into the organ is permitted whereas the return flow of blood out of the organ into the body is restricted. This will result in an erection of the organ in many cases, and is also effective in permitting longer retention of an erection once it has been obtained, wherein the penile constriction device will then be effective in retaining the erection as long as may be necessary.

It is an object of the present invention, to improve a penile constriction device for a better application during sexual intercourse.

In order to achieve the above and further objects, according to the present invention, there is provided a penile constriction device comprising a ring-shaped body, further comprising a head element provided at said ring-shaped body and protruding away therefrom.

By means of the present invention the device allows for a special stimulation of the female clitoris during sexual intercourse. This is achieved in that the ring-shaped body is provided with a head element which is adapted to act as a clitoral stimulation means. The head element is to be dimensioned by considering the distance to the clitoris when the head element is in a centrally upright position. In particular, the head element is to be dimensioned so that it is able to more or less directly contact the female clitoris. As the element protrudes away from the ring-shaped body, the head element may be considered a top piece and therefore may be alternatively called top piece. So, according to the present invention the device combines a basic ring-shape with a top piece which is defined by the head element.

After all, the penile constriction device according to the present invention has at least dual purpose, i.e. it is provided not only for a longer retention of an erection of the male organ, but also for a stimulation of the female clitoris during sexual intercourse. So, due to the provision of a head element having a certain shape, the function of the penile constriction device is extended.

The head element may be removably attached to said ring-shaped body. So, it is allowed for an exchange of the head element in order to select among different specific head elements according to individual preferences and to adapt the use of the head element to the individual dimensions of the human body. Hence, it is offered the option to provide a plurality of different head elements in particular having different shape and/or function among which the head element with the desired shape/and function is selected for the current use. However, as a further alternative also covered by the present invention, the head element may be fixedly and constantly attached to the ring-shaped body without being removable, too.

Further advantageous embodiments and modifications of the present invention are defined in the dependent claims.

According to a preferred embodiment, said head element is provided at an outer periphery portion of said ring-shaped body. This results in an optimum arrangement of said head element for acting as a clitoral stimulation means. In a modification of this embodiment, said head element is provided to extend in an essentially radial direction relative to said ring-shaped body.

According to a further preferred embodiment, said ring-shaped body is provided with a first coupling means, said head element comprises a second coupling means, and said first and second coupling means are adapted to removably mount the head element to said ring-shaped body. Said first coupling means may be provided as a protruding portion extending away from said ring-shaped body, and said second coupling means defines an opening in the head element adapted to accommodate said protruding portion. Advantageously, the cross section of the opening essentially corresponds to the cross section of the protruding portion so as to achieve a non-rotatable and safe coupling of the head element to the ring-shaped body so that the head element cannot twist relative to the ring-shaped body, but remains in its desired position; however, alternative measures can be provided for realizing a non-rotatable and safe coupling of the head element to the ring-shaped body. Preferably, the opening can have a rectangular or quadratic cross section. So, the protruding element is somewhat like a protrusion or extension extending away from the ring-shaped body and is provided like a socket or plug onto which the head element is mounted by inserting the protruding portion into the opening in the head element.

A still further preferred embodiment comprises vibration means which is at least partly included in said protruding portion. So, the protruding portion is used as a further housing for a space-saving accommodation of at least a part of the vibration means so as to transfer vibrations created by said vibration means into the organ for enhancing stimulation.

In a further modification of the aforementioned embodiment, said first coupling means is adapted to transfer vibrations created by said vibration means to the second coupling means and, hence, to said head element. This modification has the advantage of an enhanced stimulation not only of the penis but also of the female clitoris via the head element.

In a still further advantageous modification of the aforementioned embodiment, a switch for switching on and off said vibration means is provided at the outer surface of the protruding portion of said ring-shaped body, and said head element comprises a button portion which is positioned so as to be in alignment with said switch when the head element is mounted at the protruding portion of the ring-shaped body. This modification allows for a space-saving arrangement of the switch without affecting the shape and size of the ring-shaped body. With the head element mounted at the protruding portion, the pressing of the button portion results in an actuation of the switch which is arranged directly below the button portion. Of course, the button portion must be movably arranged in the head element. If the button portion is integral with the remainder of the head element, the material of the head element should be flexible or elastic at least in the area of said button portion.

According to a still further modification of the aforementioned embodiment, said protruding portion includes a battery and said first coupling means includes an electrical connector for connection of an electrical cable for charging the battery. So, the first coupling means can be advantageously used for accommodation of an electrical connector provided for connection of an electrical cable so as to charge the battery, without affecting the ring-shaped body and in particular its size. The electrical connector is to be positioned at said first coupling means so that, when the head element is mounted at said first coupling means, the electrical connector is to be covered by said second coupling means of said head element, which is another advantage since the electrical connector is 'optically' hidden and, hence, does not affect the design of the whole device and further is protected against harmful environmental influences like liquid, moisture or dust.

So, the head element acts somewhat like a cap or cover for the electrical connector.

Preferably, said head element is formed like a finger which may be arranged so as e.g. to be bent towards the clitoris or the testicles.

According to a still further preferred embodiment, said head element is essentially Y-shaped. A Y-shape is advantageous for special stimulation of the female clitoris to be positioned between both legs of such a Y-shaped head element.

According to a still further preferred embodiment, said head element comprises a bent portion and/or a bent and/or rounded end portion which is particularly advantageous for better reaching the clitoris or the testicles.

Preferably the head element can be made of hard or rigid material or at least comprise a hard surface by using ABS plastics which is very suitable to transfer vibrations from the vibrations means for a better clitoral stimulation. Alternatively, the head element can be essentially made of flexible or elastic material, in particular flexible silicon, which may comprise a soft vibrating surface.

Preferably, said ring-shaped body is essentially made of an elastic material, in particular elastic silicon, which may comprise a soft vibrating surface adapted to better transfer vibrations created by the vibration means for a better stimulation of the penis.

According to a still further preferred embodiment, said ring-shaped body is an essentially elastic two-components body.

In the following, preferred embodiments according to the present invention will be described with reference to the accompanying drawings in which.

Figure 1:
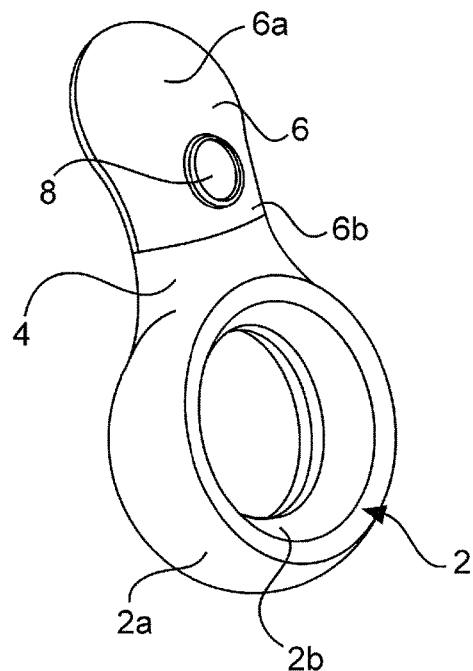
FIG. 1 is a perspective side view of a penile constriction device according to a preferred embodiment of the present invention in a completely assembled state.
Figure 2:
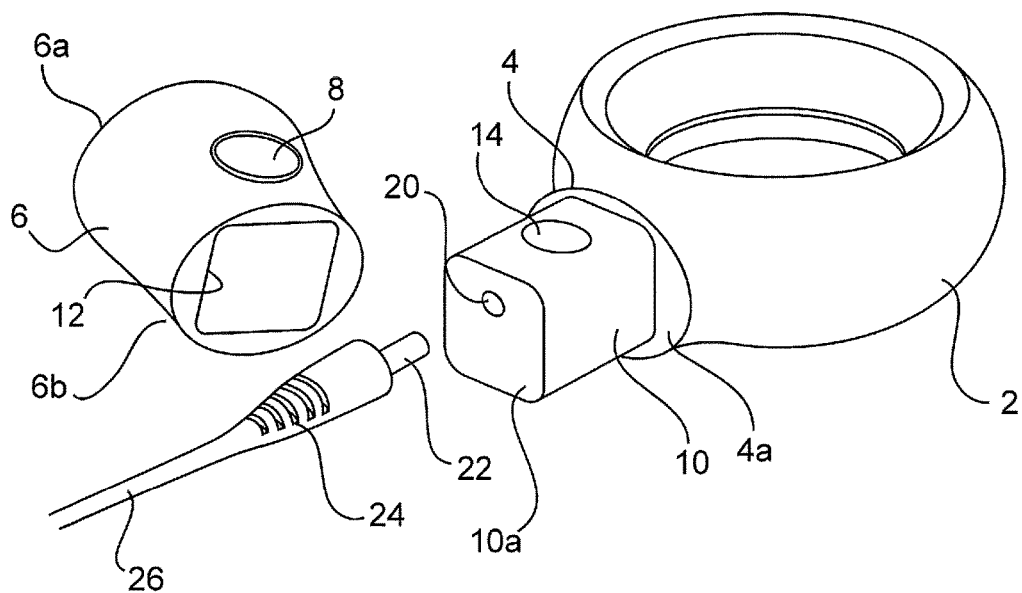
FIG. 2 is another perspective view of the penile constriction device of FIG. 1 with a head element being separated from a ring-shaped body and an electrical cable additionally shown.
Figure 3:
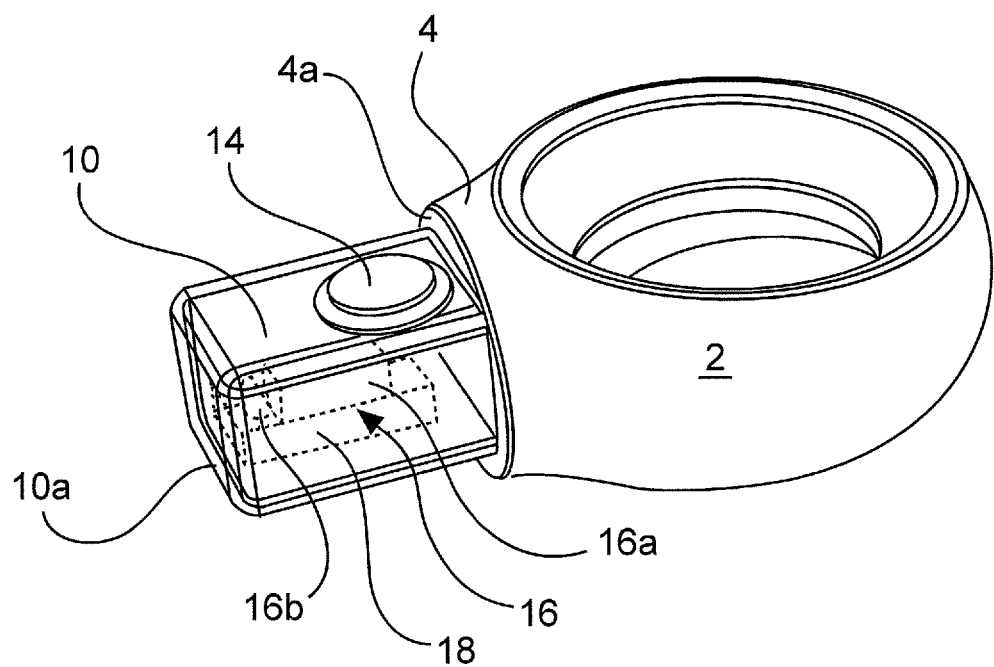
Figure 4:
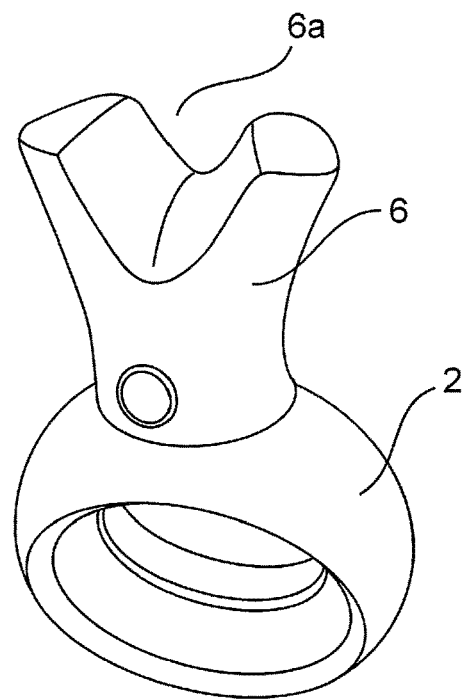
Figure 5:
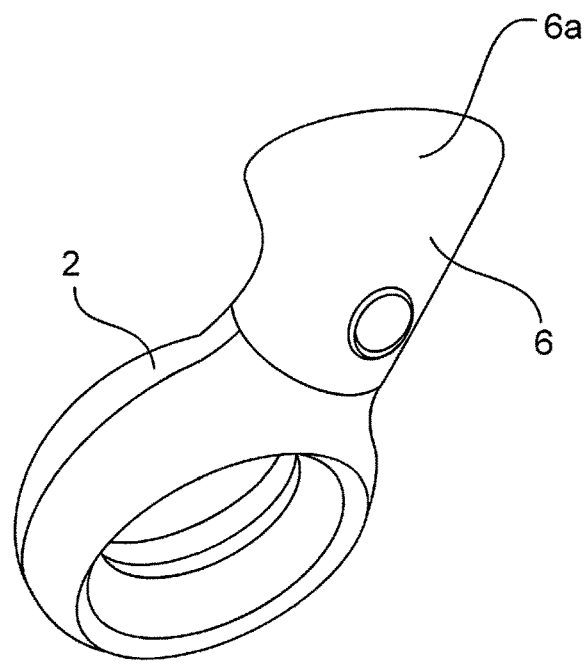

FIG. 3 a perspective view similar to that of FIG. 2, but without the illustration of the head element and the electrical cable, wherein a vibration means and a battery included in a male connector are shown in dotted lines;

FIG. 4 is another perspective view of the penile constriction device according to a preferred embodiment of the present invention in a completely assembled state with a head element according to a first preferred modification over the head element of the penile constriction device of FIG. 1; and FIG. 5 is another perspective view of the penile constriction device according to a preferred embodiment of the present invention in a completely assembled state with a head element according to a second preferred modification over the head element of the penile constriction device of FIG. 1.

FIG. 1 shows a penile constriction device according to a preferred embodiment of the present invention in a completely assembled state which is also the operational mode. The penile constriction device comprises a ring-shaped body 2 whose construction and function corresponds to a conventional penile constriction ring. In the shown embodiment, the body 2 forms an elastic two-components main body having an outer peripheral portion 2a and an inner portion 2b. Both portions 2a, 2b may differ in material and/or colour.

In particular, at least the surface or skin of both portions 2a, 2b may consist of elastic silicone or both portions 2a, 2b essentially in their entirety may be made of elastic silicone.

A socket 4 is arranged on the outer portion 2a of the body 2 and forms a protrusion extending radially from the ring-shaped body 2. The penile constriction device further comprises a head element 6 which, in its operational mode as shown in FIG. 1, is to be placed upon the socket 4 of the ring-shaped body 2 so as to be in alignment with the socket 4 and to extend in a radial direction relative to the ring-shaped body 2 in the same manner as the socket 4. So, the head element 6 comprises a distal free end portion 6a and is arranged with its proximal end 6b on the socket 4. As further shown in FIG. 1, the surface of the head element 6 includes a specific portion which is provided as a button portion 8 to be explained below in greater detail and, in the shown embodiment, has a circular shape.

FIG. 2 shows the head element 6 disconnected from the socket 4 of the ring-shaped body 2 and, hence, from the body 2 itself. So, in the described embodiment, the mounting of the head element 6 to the socket 4 of the body 2 is releasable. As shown in FIG. 2, a male connector 10 is arranged at an end face 4a of the socket 4. In the shown embodiment, the male connector 10 is formed as a rectangular-shaped block having a rectangular or quadratic cross section, which block radially protrudes away from the socket 4. As further shown in FIG. 2, the head element 6 includes a cavity or opening 12 which opens at its proximal end 6b. The cavity or opening 12 has dimensions corresponding to the dimensions of the male connector 10 and, in particular, has a cross-section corresponding to the cross-section of the male connector 10. Accordingly, the male connector 10 at the socket 4 of the body 2 and the opening 12 in the head element 6 are shaped such that the male connector 10 fits into the opening 12 and, hence, the opening 12 of the head element 6 is provided as a female connector for accommodating the male connector 10 in a non-rotatable manner so as to fixedly mount the head element 6 to the socket 4 of the body 2. So, the male connector 10 at the body 2 and the opening 12 in the head element 6 are provided as first and second coupling means which are adapted to removably mount the head element 6 to the ring-shaped body 2. The male connector 10 and the opening 12 comprise complementary engaging portions (not shown in the figures) which are adapted to provide between the head element 6 and the socket 4 of the body 2 a tight coupling which, however, is releasable. In particular, said engaging portions may comprise releasably arresting means.

As further shown in FIG. 2, a switch 14 is provided at a side surface of the male connector 10. The male connector 10 and the opening 12 are shaped and the button portion 8 at the head element 6 and the switch 14 at the male connector 10 are arranged such that the button portion 8 at the head element 6 is positioned directly above and in alignment with the switch 14 when the head element 6 is mounted to the socket 4 of the body 2 with the male connector 10 being accommodated within the opening 12 of the head element 6. Pressing of the button portion 8 at the head element 6 down to the male connector 10 results in an actuation of the switch 14 at the male connector 10. In order to transfer the forces created by pressing the button portion 8 to the switch 14, the head element 6 comprises flexible or elastic material like silicone at least in the area of the button portion 8.

As shown in FIG. 3 by dotted lines, there are further provided a vibration means 16 and a chargeable battery 18. In the shown embodiment, the vibration means 16 and the battery 18 are accommodated within the male connector 10, wherein the vibration means 16 comprises an electrical motor 16a and an excenter 16b rotatively driven by the electrical motor 16a for creating vibrations. The male connector 10 is adapted for transferring the vibrations from the vibrations means 16 into the head element 6 as well as into the body 2. Whereas, in the shown embodiment, the vibration means 16 and the battery 18 are completely accommodated within the male connector 10, alternatively at least one of these components maybe partly or completely arranged within the socket 4 and/or the ring-shaped body 2.

The vibration means 16 is supplied with electrical power by the battery 18 and to be activated or deactivated by the switch 14 which is, thus, provided as an on/off switch. The battery is connected to an electrical socket 20 provided in the end face 10a of the male connector 10, as further shown in FIG. 2. The socket 20 is adapted to accommodate a lug jack 22 of an electrical plug 24 coupled with a cable 26 in order to connect the chargeable battery 18 to an external electrical charging device (not shown) for charging. FIG. 2 shows the electrical plug 24 with its cable 26 disconnected from the socket 20.

The head element 6 according to the embodiment shown in FIGS. 1 and 2 is formed like a finger with a rounded end portion 6a. Since the head element 6 is removable from the male connector 10 and, hence, from the ring-shaped body 2, there is an option to use other head elements 6 in particular with different shape. FIG. 4 shows mounted at the body 2 a head element 6 according to an alternative modification with the distal end portion 6a of the head element 6 having a Y-shape for special stimulation of the clitoris. FIG. 5 shows a still further modification of the head element 6 which is formed like a finger having a bent end portion 6a to be directed, with the penile constriction device in use, either towards the clitoris or towards the testicles for stimulation accordingly.

Preferably, the head element 6 or at least its surface is made of hard or rigid material, preferably ABS plastics. Alternatively, the head element 6 or at least its surface can be made of flexible or elastic material, preferably flexible silicone.

The invention claimed is:

1. A penile constriction device comprising:
a ring-shaped body and an elongated head element having a length that is greater than its maximum width, wherein the head element extends lengthwise in a radial direction relative to the ring-shaped body;
wherein the ring-shaped body has an interior diameter sized to closely encircle a penis, and the head element is removably attached to the ring-shaped body; and
wherein the head element is disposed so that the head element can contact a clitoris during sexual intercourse when the ring-shaped body is positioned on the penis;
wherein the ring-shaped body has an outer peripheral portion at which the head element is provided;
wherein the head element extends in an essentially radial direction relative to the ring-shaped body;
wherein the ring-shaped body is provided with a coupling means for removably mounting the head element to the ring-shaped body; and
wherein the coupling means comprises a protruding portion extending away from the ring-shaped body and wherein the head element includes an opening adapted to accommodate the protruding portion.

2. The device according to claim 1, wherein the opening has a cross section that essentially corresponds to a cross section of the protruding portion.

3. The device according to claim 2, wherein the opening has a rectangular or quadratic cross section.

4. The device according to claim 1, wherein the protruding portion at least partly includes a motor configured to create vibrations.

5. The device according to claim 4 wherein the coupling means is adapted to transfer vibrations created by the motor to the head element.

6. The device according to claim 4 wherein a switch configured to switch on and off the motor is provided at an outer surface of the protruding portion of the ring-shaped body, and the head element comprises a button portion positioned so that it is essentially in alignment with the switch when the head element is coupled to the protruding portion.

7. The device according to claim 1 wherein the protruding portion includes a battery and the coupling means includes an electrical connector for connection of an electrical cable for charging the battery.

8. The device according to claim 1 wherein the head element is formed like a finger.

9. The device according to claim 1 wherein the head element comprises a bent portion.

10. The device according to claim 1 wherein the head element comprises a bent end portion or a rounded end portion.

11. The device according to claim 1 wherein the head element comprises a flexible or elastic material.

12. The device according to claim 1 wherein the head element comprises a hard or rigid material.

13. The device according to claim 1, wherein the ring-shaped body comprises an elastic material.

14. The device according to claim 1, wherein the ring-shaped body has a first component comprising an outer peripheral portion and a second component comprising an inner portion and wherein at least one of the first and second components comprises an elastic material.

15. The device according to claim 11 wherein the flexible or elastic material comprises flexible silicon.

16. The device according to claim 12 wherein the hard or rigid material comprises an ABS plastic.

17. The device according to claim 13 wherein the elastic material comprises silicon.

18. A penile constriction device comprising:
a ring-shaped body and an elongated head element having a length that is greater than its maximum width, wherein the head element extends lengthwise in a radial direction relative to the ring-shaped body;
wherein the ring-shaped body has an interior diameter sized to closely encircle a penis, and the head element is removably attached to the ring-shaped body;
wherein the head element is disposed so that it the head element can contact a clitoris during sexual intercourse when the ring-shaped body is positioned on the penis; and
wherein the head element is essentially Y-shaped and has arms that diverge away from the ring-shaped body.

19. A penile constriction device comprising:
a ring-shaped body;
a head element removably disposed on and protruding away from the ring-shaped body, wherein the head element has a length that is greater than its maximum width; and
a motor configured to create vibrations to be transferred to the head element;
wherein the ring-shaped body is adapted to closely encircle a penis;
wherein the head element extends lengthwise in an essentially radial direction relative to the ring-shaped body and is dimensioned to contact a clitoris during sexual intercourse when the ring-shaped body is positioned on the penis;

wherein the head element is removably attached to the ring-shaped body; and wherein the ring-shaped body includes a coupling portion that extends away from the ring-shaped body and is adapted to mate with an opening in the head element.

20. The device according to claim 19 further comprising a switch configured to switch on and off the motor, wherein the switch includes a button positioned on the head element.

\* \* \* \* \*